(12) United States Patent
Haick et al.

(10) Patent No.: US 8,903,661 B2
(45) Date of Patent: Dec. 2, 2014

(54) CHEMICAL SENSORS BASED ON CUBIC NANOPARTICLES CAPPED WITH AN ORGANIC COATING FOR DETECTING EXPLOSIVES

(75) Inventors: Hossam Haick, Haifa (IL); Ekaterina Dovgolevsky, Haifa (IL)

(73) Assignee: Technion Research and Development Foundation Ltd., Haifa (IL)

( * ) Notice: Subject to any disclaimer, the term of this patent is extended or adjusted under 35 U.S.C. 154(b) by 1080 days.

(21) Appl. No.: 12/933,439

(22) PCT Filed: Mar. 26, 2009

(86) PCT No.: PCT/IL2009/000342
§ 371 (c)(1),
(2), (4) Date: Sep. 20, 2010

(87) PCT Pub. No.: WO2009/118739
PCT Pub. Date: Oct. 1, 2009

(65) Prior Publication Data
US 2011/0015872 A1    Jan. 20, 2011

(30) Foreign Application Priority Data
Mar. 27, 2008    (IL) .......................................... 190475

(51) Int. Cl.
*G01N 33/22*    (2006.01)
*G01N 33/00*    (2006.01)
*B82Y 15/00*    (2011.01)
*B82Y 30/00*    (2011.01)
(52) U.S. Cl.
CPC ............ *G01N 33/0057* (2013.01); *B82Y 15/00* (2013.01); *B82Y 30/00* (2013.01)
USPC ............................... 702/22; 702/30; 436/106

(58) Field of Classification Search
USPC ............ 702/22–25, 27, 30, 32; 436/103, 106, 436/110; 428/119
See application file for complete search history.

(56) References Cited

U.S. PATENT DOCUMENTS

| 5,092,218 A | 3/1992 | Fine |
| 5,109,691 A | 5/1992 | Corrigan |

(Continued)

FOREIGN PATENT DOCUMENTS

| EP | 1215485 | 6/2002 |
| EP | 1278061 | 1/2003 |

(Continued)

OTHER PUBLICATIONS

Han L. et al., "Nanoparticle-Structured Sensing Array Materials and Pattern Recognition for VOC Detection", Apr. 29, 2005, Sensors and Actuators B, vol. 106, No. 1, pp. 431-441.*
Ahmadi et al., (1996) "Cubic" Colloidal Platinum Nanoparticles. Chem Mater 8(6): 1161-3.

(Continued)

*Primary Examiner* — Manuel L Barbee
(74) *Attorney, Agent, or Firm* — Roach Brown McCarthy & Gruber, P.C.; Kevin D. McCarthy (57) ABSTRACT

The present application describes a sensor apparatus, especially an electronic nose, based on 2D films or 3D assemblies of cubic nanoparticles capped with an organic coating. The organic coating is modified with unique compositions of functional moieties, e.g. cyclodextrins, to provide the detection of volatile and non-volatile compounds derived from explosive materials, e.g. PETN, RDX, TNT etc. with very high sensitivity. The nose employs pattern recognition algorithms and methods, e.g. PCA, for detecting and quantifying specific explosive compounds.

23 Claims, 7 Drawing Sheets

(56) References Cited

U.S. PATENT DOCUMENTS

| | | | |
|---|---|---|---|
| 5,571,401 | A | 11/1996 | Lewis |
| 5,585,575 | A | 12/1996 | Corrigan |
| 5,698,089 | A | 12/1997 | Lewis |
| 5,801,297 | A | 9/1998 | Mifsud |
| 6,010,616 | A | 1/2000 | Lewis |
| 6,316,268 | B1 * | 11/2001 | Yang et al. .................. 436/106 |
| 6,319,724 | B1 | 11/2001 | Lewis |
| 6,379,622 | B1 | 4/2002 | Polak |
| 6,411,905 | B1 | 6/2002 | Guoliang |
| 6,467,333 | B2 | 10/2002 | Lewis |
| 6,537,498 | B1 | 3/2003 | Lewis |
| 6,541,617 | B1 | 4/2003 | Bamdad |
| 6,571,649 | B2 | 6/2003 | Sakairi |
| 6,606,566 | B1 | 8/2003 | Sunshine |
| 6,609,068 | B2 | 8/2003 | Cranley |
| 6,620,109 | B2 | 9/2003 | Hanson |
| 6,746,960 | B2 | 6/2004 | Goodman |
| 6,759,010 | B2 | 7/2004 | Lewis |
| 6,767,732 | B2 | 7/2004 | Alocilja |
| 6,773,926 | B1 | 8/2004 | Freund |
| 6,820,012 | B2 | 11/2004 | Sunshine |
| 6,839,636 | B1 | 1/2005 | Sunshine |
| 6,840,120 | B2 | 1/2005 | Sakairi |
| 6,841,391 | B2 | 1/2005 | Lewis |
| 6,872,786 | B2 | 3/2005 | Murray |
| 7,034,677 | B2 | 4/2006 | Steinthal |
| 7,052,854 | B2 | 5/2006 | Melker |
| 7,144,553 | B2 | 12/2006 | Lewis |
| 7,171,312 | B2 | 1/2007 | Steinthal |
| 7,186,381 | B2 | 3/2007 | Penner |
| 7,224,345 | B2 | 5/2007 | Kawell |
| 7,482,067 | B2 | 1/2009 | Sohn |
| 2001/0041366 | A1 | 11/2001 | Lewis |
| 2003/0159927 | A1 | 8/2003 | Lewis |
| 2003/0198956 | A1 | 10/2003 | Makowski |
| 2004/0033165 | A1 | 2/2004 | Lewis |
| 2004/0204915 | A1 | 10/2004 | Steinthal |
| 2005/0150778 | A1 | 7/2005 | Lewis |
| 2005/0241935 | A1 | 11/2005 | Lewis |
| 2005/0263394 | A1 | 12/2005 | Lewis |
| 2006/0034731 | A1 | 2/2006 | Lewis |
| 2006/0040318 | A1 | 2/2006 | Melker |
| 2006/0160134 | A1 | 7/2006 | Melker |
| 2007/0059211 | A1 | 3/2007 | Edmiston |
| 2007/0114138 | A1 | 5/2007 | Krasteva |
| 2007/0127164 | A1 | 6/2007 | Ofek |
| 2007/0132043 | A1 | 6/2007 | Bradley |
| 2007/0165217 | A1 | 7/2007 | Johansson |
| 2007/0231790 | A1 | 10/2007 | Su |
| 2007/0264719 | A1 | 11/2007 | Santra |
| 2008/0077331 | A1 | 3/2008 | Lewis |

FOREIGN PATENT DOCUMENTS

| | | |
|---|---|---|
| FR | 2783051 | 3/2000 |
| WO | 99/27357 | 6/1999 |
| WO | 00/00808 | 1/2000 |
| WO | 2005/059952 | 6/2005 |
| WO | WO 2005/059952 A2 * | 6/2005 |
| WO | 2006/131400 | 12/2006 |
| WO | 2009/066293 | 5/2009 |

OTHER PUBLICATIONS

Chen et al.,: "Ellipsometrically probed plasmonic resonances in a square array of Au nanocubes" CLEO '07. 2007 Conference on Lasers and Electro-Optics May 5-11, 2007 Baltimore, MD, USA, Piscataway, NJ, USA, May 1, 2007, pp. 1-2.

Dovgolevsky and Haick (2008) Direct observation of the transition point between quasi-spherical and cubic nanoparticles in a two-step seed-mediated growth method. Small, 4(11):2059-66.

Dovgolevsky et al., (2009) Chemically sensitive resistors based on monolayer-capped cubic nanoparticles: towards configurable nanoporous sensors. Small 5(10): 1158-1161.

Evans et al., (2000) Vapour sensing using hybrid organic-inorganic nanostructured materials. J Mater Chem 10(1): 183-8.

Haick (2007) Journal of Physics D: Applied Physics 40(23): 7173-7186.

Han et al., (2005) Nanoparticle-structured sensing array materials and pattern recognition for VOC detection. Sensors and Actuators B 106(1): 431-441.

Joseph et al., (2008) Gold Nanoparticle/Organic Networks as Chemiresistor Coatings: The Effect of Film Morphology on Vapor Sensitivity. J Phys Chem C 112(32): 12507-14.

Li et al., (2004) Simple method for preparation of cubic Ag nanoparticles and their self-assembled films. Thin Solid Films 460(1-2): 78-82.

Lisiecki (2005) Size, shape, and structural control of metallic nanocrystals. J Phys Chem B 109(25): 12231-44.

Narayanan and El-Sayed (2003) Effect of Catalytic Activity on the Metallic Nanoparticle Size Distribution: Electron-Transfer Reaction between Fe(CN)6 and Thiosulfate Ions Catalyzed by PVP—Platinum Nanoparticles. J Phys Chem B 107(45): 12416-24.

Narayanan and El-Sayed (2004) Effect of Nanocatalysis in Colloidal Solution on the Tetrahedral and Cubic Nanoparticle Shape: Electron-Transfer Reaction Catalyzed by Platinum Nanoparticles. J Phys Chem B 108(18): 5726-33.

Sau and Murphy (2004) Room temperature, high-yield synthesis of multiple shapes of gold nanoparticles in aqueous solution. J Am Chem Soc 126(28): 8648-9.

Sherry et al., (2005) Localized surface plasmon resonance spectroscopy of single silver nanocubes. Nano Lett Am Chem Soc USA 5(10): 2034-8.

Shukla et al., (2007) Synthesis and self-assembly of magnetic nanoparticles. Surface Science 601(13): 2615-7.

Sirbuly et al., (2007) Multifunctional nanowire evanescent wave optical sensors. Adv Mater 19(1): 61-6.

Sun and Xia (2003) Gold and silver nanoparticles: a class of chromophores with colors tunable in the range from 400 to 750 nm. The Analyst 128(6): 686-91.

Wang (2004) Microchip devices for detecting terrorist weapons. Analytica Chimica Acta 507: 3-10.

Wiley et al., (2005) Shape-controlled synthesis of metal nanostructyres: the case of silver. Chem Eur J 11: 454-463.

Wohltjen and Snow (1998) Colloidal metal-insulator-metal ensemble chemiresistor sensor. Anal Chem 70(14): 2856-9.

Xiangfeng et al., (2007) The preparation and gas-sensing properties of NiFe2O4 nanocubes and nanorods. Sensors and Actuators B 123(2): 793-7.

Zhao et al., (1997) Soft lithographic methods for nano-fabrication. J Mater Chem 7(7): 1069-74.

* cited by examiner

CHEMICAL SENSORS BASED ON CUBIC NANOPARTICLES CAPPED WITH AN ORGANIC COATING FOR DETECTING EXPLOSIVES

REFERENCE TO CO-PENDING APPLICATIONS

Priority is claimed as a U.S. national entry under 35 U.S.C. 371 of PCT/IL2009/000342, filed on Mar. 26, 2009; which claims priority to Israeli patent application no. 190475, filed on Mar. 27, 2008.

FIELD OF THE INVENTION

The present invention relates to an apparatus comprising sensors of cubic nanoparticles capped with an organic coating. In particular, the apparatus is designed to detect minute concentrations of volatile and non-volatile compounds derived from explosive materials with very high sensitivity.

BACKGROUND OF THE INVENTION

The hitherto known methods for detecting explosive materials are mainly directed towards the detection of nitrogen containing compounds. These methods usually require concentrating vapors of explosive nitro-compounds followed by their decomposition to produce gases of nitric oxide (NO) and/or nitric dioxide ($NO_2$). These gases can subsequently be detected using a variety of techniques including gas, capillary electrophoresis and high performance liquid chromatography, mass spectrometry, and ion mobility analyzer. U.S. Pat. Nos. 5,092,218; 5,109,691; 6,571,649; and 6,840,120 disclose exemplary uses of said techniques for explosive detection.

Other commonly used techniques include x-ray scattering, neutron analysis, nuclear quadrupole resonance, FTIR and Raman spectrometry, and immunoassays (Wang, *Analy. Chimi. Acta,* 2004, 507: 3). U.S. Pat. No. 5,801,297 discloses methods and devices for the detection of odorous substances including explosives comprising a plurality of gas sensors selected from semiconductor gas sensors, conductive polymer gas sensors, and acoustic surface wave gas sensors. U.S. Pat. No. 6,872,786 discloses a molecularly imprinted polymeric explosives sensor, which possesses selective binding affinity for explosives. U.S. Pat. No. 5,585,575 discloses an explosive detection screening system which comprises a concentration and analyzing system for the purification of the collected vapor and/or particulate emissions and their subsequent detailed chemical analysis. U.S. Pat. No. 7,224,345 discloses a system for electrochemical detection based on carbon or carbon/gold working electrode having a modified surface to detect trace amounts of nitro-aromatic compounds.

The most frequently used sensing devices for detecting explosive materials are based on the lock-and-key approach, wherein each sensor detects one explosive material. In this manner, the sensors are designed to detect very specific target molecules resulting in restricted applicability.

Electronic nose devices perform odor detection through the use of an array of cross-reactive sensors in conjunction with pattern recognition methods. In contrast to the "lock-and-key" model, each sensor in the electronic nose device is widely responsive to a variety of odorants. In this architecture, each analyte produces a distinct signature from the array of broadly cross-reactive sensors. This configuration allows to considerably widen the variety of compounds to which a given matrix is sensitive, to increase the degree of component identification and, in specific cases, to perform an analysis of individual components in complex multi-component mixtures. Pattern recognition algorithms can then be applied to the entire set of signals, obtained simultaneously from all the sensors in the array, in order to glean information on the identity, properties and concentration of the vapor exposed to the sensor array.

Nanoparticles possess several features which render them advantageous as sensing devices designated for explosive detection. A particularly important feature is their enhanced surface to bulk ratio. Furthermore, molecules that are attached to the surface of the nanoparticles play a key role in determining the physical and chemical properties of these particles. Such molecules are often referred to as organic coating that can be tailored to serve either one of several functionalities. Most importantly, the organic coating can modify the electronic properties of "bare" nanoparticles. It is further possible to obtain electron transport between the nanoparticles and the organic coating thus introducing cooperative effects. Nanoparticles capped with an organic coating (NPCOC) are therefore of high technological importance, particularly since both nanoparticles and their organic coating may be selected from a wide variety of compounds.

Devices based on nanoparticles and methods of use thereof for detecting, inter alfa, explosive compounds are disclosed in e.g. U.S. Pat. Nos. 7,171,312; 7,144,553; 7,034,677; 6,839,636; 6,773,926; 6,759,010; in U.S. Patent Application Nos. 2007/0264719; 2007/0231790; 2007/0165217; 2007/0132043; 2007/0059211; 2006/0160134; 2006/0040318; 2005/0263394; 2005/0150778; 2004/0204915 and 2001/0041366 and in Wohltjen et al., *Anal. Chem.,* 1998, 70(14): 2856; and Evans et al., *J. Mater. Chem.,* 2000, 10(1): 183.

U.S. Pat. No. 7,052,854 discloses systems and methods for detecting a target analyte/biomarker including an explosive, using nanostructure-based assemblies comprising a nanoparticle, a means for detecting a target analyte/biomarker, and a surrogate marker. The sensor technology is based on the detection of the surrogate marker which indicates the presence of the target analyte/biomarker in a sample.

Sensors based on changes in the physical and/or electrical properties of films composed of spherical NPCOC(SNP-COC) have been illustrated in the literature. Theoretical as well as experimental measurements indicate that the sensitivity of SNPCOC based sensors toward analytes is limited to a concentration range of 100-1000 parts per billion (ppb). This limitation has been attributed to two main reasons. First, while voids between adjacent (spherical) nanoparticles can host analyte molecules during the exposure process, they do not contribute to the obtained sensing signal. Second, the contact interface between adjacent spherical nanoparticles, onto which analyte molecules adsorb and induce sensing signals (e.g., by inducing swelling/aggregation of the film), is limited to a very small area in comparison to the total surface area of the SNPCOCs.

For the reasons mentioned hereinabove, obtaining high sensing performance requires increased sensitivity which is often met by pre-concentrating the explosive vapors prior to their measurement thus leading to lengthier measurements. Alternatively, in order to achieve high sensitivity, an increase in film thickness can be employed. However, such an increase results in intensified diffusion limitations, thus reducing the response time. Hence, there is an unmet need for fast responsive sensors having improved sensitivity as well as selectivity allowing real-time measurement of minute quantities of volatile or non-volatile compounds derived from explosive materials.

SUMMARY OF THE INVENTION

The present invention provides an apparatus for detecting volatile and non-volatile compounds derived from explosive materials with very high sensitivity. The apparatus disclosed herein comprises cubic nanoparticles capped with an organic coating (cubic NPCOCs) wherein the organic coating comprises unique compositions of amine, imine, amide, ammonium, keto, alcohol, ester, cyclodextrin, phosphate, thiol, sulfonate, sulfonyl and/or carboxyl moieties, particularly suitable for binding to explosive materials and decomposition fragments thereof. Within the scope of the present invention is a system comprising the apparatus in conjunction with a learning and pattern recognition analyzer. The learning and pattern recognition analyzer receives sensor output signals and compares them to stored data using algorithms such as artificial neural networks and principal component analysis. The present invention further provides methods of use of the apparatus and system of the present invention for detecting and quantifying compounds derived from explosive materials.

The present invention is based in part on the unexpected finding that nanoparticles having cubic morphology are particularly advantageous for sensing applications due to the low fraction of voids in 2D or 3D structure assemblies. In particular, nowhere in the background art is it disclosed or suggested that cubic nanoparticles capped with an organic coating can be advantageous for use as highly sensitive sensors for explosive detection in comparison to nanoparticle-based sensors with other geometries. The increased interface contacts between adjacent conductive cubic particles as compared to particles having a spherical geometry enhance the efficacy of electron transfer to provide improved signal to noise ratios. Another advantage stems from the vertexes/edges of cubic nanoparticles which exhibit higher field effects as compared to smooth surface geometries. Additionally, the cubic nanoparticles of the present invention are capped with unique compositions of organic coating, specifically designed for the detection of explosives.

According to a first aspect, the present invention provides an apparatus for detecting volatile and non-volatile compounds derived from explosive materials, comprising at least one chemically sensitive sensor comprising cubic nanoparticle conductive cores capped with an organic coating, wherein the organic coating comprises a backbone and at least a first functional moiety and a second functional moiety bound to said backbone, wherein the first functional moiety is further bound to the nanoparticle conductive cores.

According to a second aspect, the present invention provides a system for detecting volatile and non-volatile compounds derived from explosive materials, comprising i) an apparatus comprising an array of chemically sensitive sensors of cubic nanoparticle conductive cores capped with an organic coating, wherein the organic coating comprises a backbone and at least a first functional moiety and a second functional moiety bound to said backbone, wherein the first functional moiety is further bound to the nanoparticle conductive cores, and ii) a learning and pattern recognition analyzer wherein the learning and pattern recognition analyzer receives sensor signal outputs and compares them to stored data.

According to one embodiment, the apparatus and system of the present invention detect volatile and non-volatile compounds derived from explosive materials with sensitivity of less than one part per million (ppm). According to another embodiment, the apparatus and system of the present invention detect volatile and non-volatile compounds derived from explosive materials with sensitivity of less than 100 parts per billion (ppb). According to yet another embodiment, the apparatus and system of the present invention detect volatile and non-volatile compounds derived from explosive materials with sensitivity of less than 10 parts per billion (ppb).

According to some embodiments, the apparatus and system disclosed herein comprise cubic nanoparticle conductive cores selected from metals and/or metal alloys. According to other embodiments, the nanoparticle conductive cores comprise metals and metal alloys selected from the group consisting of Au, Ag, Ni, Co, Pt, Pd, Cu, Al, Au/Ag, Au/Cu, Au/Ag/Cu, Au/Pt, Au/Pd, Au/Ag/Cu/Pd, Pt—Rh, Ni—Co, and Pt—Ni—Fe.

According to various embodiments, the organic coating comprises a monolayer or multilayers of organic compounds, wherein the organic compounds are selected from small molecules, monomers, oligomers and polymers. In particular embodiments, the backbone of the organic coating comprises alkyl, aryl, and alkylaryl chains. In currently preferred embodiments, the backbone of the organic coating comprises $C_3$-$C_{24}$ alkyl chains.

In certain embodiments, the first functional moiety of the organic coating comprises at least one of a thiol, a thiolate, a sulfide, a disulfide, a sulfite, a sulfate, a carbamate, an amine, a phosphine, a carboxylate, a cyanate or an isocyanate moiety. In currently preferred embodiments, the backbone of the organic coating further functionalized with the first functional moiety comprises at least one of alkylthiols with $C_3$-$C_{24}$ chains, ω-functionalized alkanethiolates, arenethiolate, (γ-mercaptopropyl)trimethyloxysilane, dialkyl disulfides and combinations thereof.

In some embodiments, the second functional moiety of the organic coating comprises at least one of an amine, an imine, an amide, an ammonium, a keto, an alcohol, an ester, a cyclodextrin, a phosphate, a thiol, a sulfonate, a sulfonyl or a carboxyl moiety.

In currently preferred embodiments, the second functional moiety is selected from the group consisting of ethyleneimine, aniline-boronic acid, diethyl ester, 2,5-dimercapterephthalic acid, n-(3-trifluoroethanesulfonyloxypropyl)-anthraquinone-2-carboxamide, thiophene, 1-[4-(4-dimethylamino-phenylazo)-3-[3,5-bis[3,5-bis[3,5-bis(3-butene-1-oxy)benzyloxy]benzyloxy]benzyloxy]phenyl]-2, 2,2 trifluoroethanone, permethylated α-cyclodextrin-$6^4$-monoalcohol nitrate, dinitrophenyl substituted β-cyclodextrin, β- and γ-CD bearing a 4-amino-7-nitrobenz-2-oxa-1,3-diazole, sulfated and carboxymethylated β-cyclodextrins, mono(6-cyclohexylamino-6-deoxy)-β-cyclodextrin, mono[6-benzyl-imino-6-deoxy]-β-cyclodextrin, mono[6-(o-aminophenyl)imino-6-deoxy]-β-cyclodextrin, mono[6-(p-aminophenyl)imino-6-deoxy]-β-cyclodextrin, mono[6-(α-naphthyl)imino-6-deoxy]-β-cyclodextrin, hexakis(6-O-benzoyl)-α-cyclodextrin, heptakis(2,3,6-tri-O-benzoyl)-β-cyclodextrin, hexakis(2,3-di-O-benzyl)-α-cyclodextrin, hexakis(6-O-benzoyl-2,3-di-O-benzyl)-α-cyclodextrin, 2- and 6-amino-β-cyclodextrin, 2A,3A-alloepithio-2A,3A-dideoxy-β-cyclodextrin and combinations thereof.

The apparatus and system according to the principles of the present invention can be configured in any configuration including, but not limited to, 1D wires, 2D films and 3D assemblies.

In some embodiments, the sensing apparatus and system of the present invention comprise sensors comprising a plurality of cubic nanoparticles capped with an organic coating, wherein the organic coating comprises a backbone and at least a first functional moiety and a second functional moiety bound to said backbone, wherein the first functional moiety is further bound to the nanoparticle conductive cores, and further comprise at least one of a chemiresistor, chemicapacitor, quartz crystal microbalance, bulk acoustic wave (BAW) and surface acoustic wave (SAW) resonator, electrochemical cell, surface plasmon resonance (SPR), and optical spectroscope.

Without being bound by any theory or mechanism of action, it is contemplated that sensing occurs via aggregation or swelling of the cubic nanoparticles capped with an organic coating assemblies, through hydrogen-bonding, π-π, host-guest, van der Waals, electrostatic, charge-transfer or via changing of permittivity upon analyte sorption.

In some embodiments, the apparatus and system of the present invention are designed to detect volatile and non-volatile compounds derived from explosive materials, wherein the explosive materials are in gas, vapor and/or liquid states.

In particular embodiments, the apparatus and system of the present invention are designed to detect minute concentrations of explosive materials selected from the group consisting of pentaerythitol tetranitrate (PETN), tetranitro-tetrazacylooctane (HMX), nitroglycerin (NG), ethylene glycol dinitrate (EGDN), $NH_4NO_3$, dinitrotoluene (DNT), trinitrotoluene (TNT), tetryl, picric acid, cyclotrimethylenetrinitramine (RDX), mixtures and fragments thereof. In other particular embodiments, the apparatus and system of the present invention are designed to detect NO and/or $NO_2$ gases derived from explosive materials.

In yet other embodiments, the system of the present invention comprises an apparatus comprising an array of chemically sensitive sensors of cubic nanoparticle conductive cores capped with an organic coating, wherein the organic coating comprises a backbone and at least a first functional moiety and a second functional moiety bound to said backbone, wherein the first functional moiety is further bound to the nanoparticle conductive cores, and a learning and pattern recognition analyzer, wherein the learning and pattern recognition analyzer receives sensor output signals and compares them to stored data. The learning and pattern recognition analyzer utilizes various algorithms including, but not limited to, artificial neural networks, multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical methods including, but not limited to, principal component analysis (PCA), partial least squares (PLS), multiple linear regression (MLR), principal component regression (PCR), discriminant function analysis (DFA) including linear discriminant analysis (LDA), and cluster analysis including nearest neighbor.

According to another aspect, the present invention provides a method for determining at least one of the composition and concentration of volatile and non-volatile compounds derived from explosive materials in a sample, comprising the steps of: (a) providing a system comprising an apparatus comprising an array of chemically sensitive sensors of cubic nanoparticle conductive cores capped with an organic coating, wherein the organic coating comprises a backbone and at least a first functional moiety and a second functional moiety bound to said backbone, wherein the first functional moiety is further bound to the nanoparticle conductive cores; and a learning and pattern recognition analyzer wherein the learning and pattern recognition analyzer receives sensor output signals and compares them to stored data; (b) exposing the sensor array of the apparatus to the sample, and (c) using pattern recognition algorithms to detect the presence of volatile and non-volatile compounds derived from explosive materials in the sample.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention provides an apparatus, which uses 1D wires, 2D films or 3D assemblies of cubic nanoparticles capped with an organic coating (cubic NPCOC) as sensors for the detection of volatile and non-volatile compounds derived from explosive materials. The invention further provides a system comprising an array of sensors of cubic nanoparticles capped with an organic coating and a learning and pattern recognition analyzer which utilizes algorithms such as principal component analysis and neural network algorithms. In particular, the cubic nanoparticle conductive cores are capped with an organic coating wherein the backbone of the organic coating is modified with unique compositions of functional groups comprising amine, imine, amide, ammonium, keto, alcohol, ester, cyclodextrin, phosphate, thiol, sulfonate, sulfonyl and/or carboxyl moieties to provide detection of explosives and compounds derived therefrom. Methods of use of the apparatus and system in detecting and classifying a wide variety of volatile and non-volatile explosive materials, mixtures and fragments thereof are further disclosed.

Without being bound by any theory or mechanism of action, sensing is obtained through adsorption of explosive compounds to provide changes in electrical properties and in particular in electrical resistance. The electrical signals are then conveyed to a learning and pattern recognition analyzer to generate qualitative identification and preferably quantitative analysis of desired explosives.

Figure 1A:
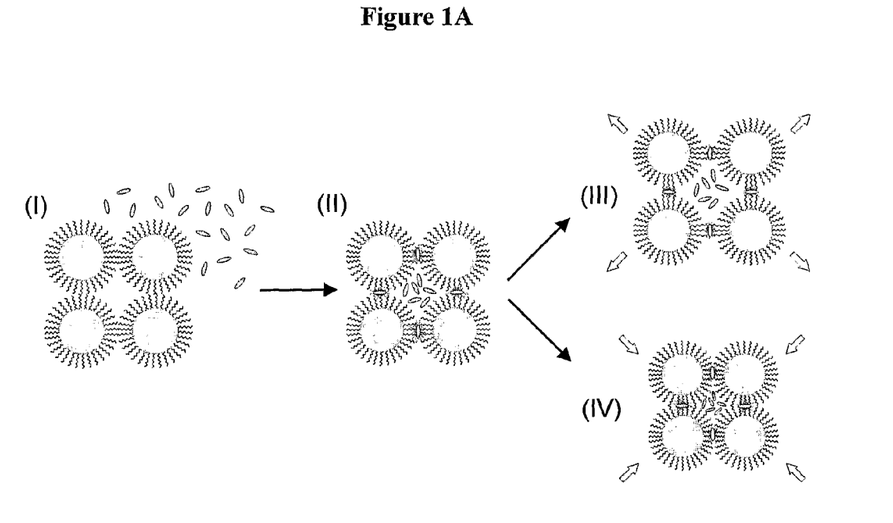
FIG. 1A. Schematic illustration of the swelling- (or aggregation)-based sensing mechanism for films/assemblies of molecularly modified spherical nanoparticles capped with an organic coating (SNPCOC) comprising the following steps: (I) before analyte adsorption, (II) after analyte adsorption, (III) swelling following analyte adsorption, or (IV) aggregation following analyte adsorption.
Figure 1B:
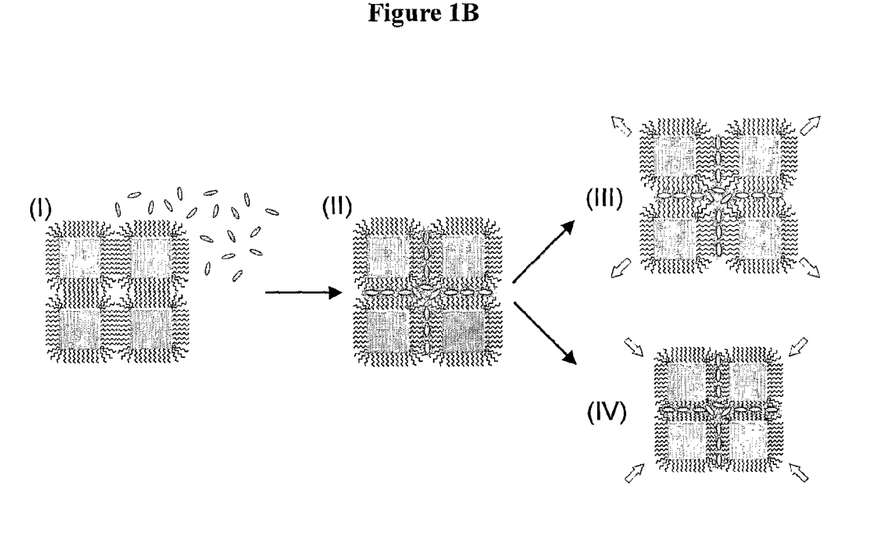
FIG. 1B. Schematic illustration of the swelling- (or aggregation)-based sensing mechanism for films/assemblies of molecularly modified cubic nanoparticles capped with an organic coating comprising the following steps: (I) before analyte adsorption, (II) after analyte adsorption, (III) swelling following analyte adsorption, or (IV) aggregation following analyte adsorption.

Upon adsorption of an analyte, the film/assembly of NPCOCs can either swell, or aggregate (see FIG. 1A & FIG. 1B (III) and (IV), respectively). In thin films of NPCOCs a relative change in the permittivity constant of the film upon analyte adsorption may be generated. This is determined by the nature of the interaction between analyte (host) species and the molecules coating the nanoparticles. As illustrated in the figures, only molecules at the interface between molecularly modified nanoparticles contribute to the swelling/aggregation. On the contrary, molecules that occupy the voids between adjacent nanoparticles, contribute little or none to the total swelling of the film. The contact interface between adjacent cubic NPCOCs (FIG. 1B), where the analyte molecules adsorb to induce sensing signals is significantly larger than that of equivalent spherical nanoparticles (FIG. 1A). A film of molecularly modified cubic nanoparticles requires lower concentration of analyte to induce a given swelling/aggregation, as compared to equivalent films based on molecularly modified spherical nanoparticles. Without being bound by ant theory or mechanism of action, the larger interface between adjacent conductive nanoparticles in cubic NPCOCs in comparison to SNPCOCs, results in an increase of the electron tunneling/hopping efficiency from one nanoparticle to another, hence lowering the background noise. Films/assemblies composed of cubic nanoparticles are thus more efficient and consequently more sensitive, in comparison to equivalent films of spherical nanoparticles (SNPCOCs).

Another important feature of cubic NPCOCs stems from structural considerations. The vertexes/edges of cubic nanoparticles exhibit higher field effects than the center of the cubic facets. Thus, non-uniform surfaces such as those which appear in cubic nanoparticles are advantageous in comparison to SNPCOCs which exhibit smooth surfaces.

It was not previously realized that cubic NPCOC sensors are more sensitive, more controlled, and more suitable to differentiate between subtle differences in mixtures of volatile and/or non-volatile explosive materials than films/assemblies of SNPCOC. Enhanced selectivity can further be achieved through modifying the binding characteristics of the capping film as well as linker molecules.

In one embodiment, the apparatus of the present invention comprises sensors of cubic NPCOCs comprising nanoparticle conductive cores capped with non-conductive organic molecules. As used herein the terms "cubic NP" or "cubic nanoparticles" may be used interchangeably, and are defined as three-dimensional solid particles, wherein each particle substantially comprises six faces, facets or sides, wherein three faces, facets or sides essentially meet at a single vertex. Alternatively each three faces, facets or sides meet a joined surface. The dimensions of a given facet range between about 0.1 to about 150 nm, and more preferably between about 1 to about 80 nm. In some embodiments, the term "cubic nanoparticles" refers to a population of nanoparticles wherein at least 50% of the particles exhibit cubic morphology. More preferably, the term "cubic nanoparticles" refers to a population of nanoparticles wherein at least 70% of the particles exhibit cubic morphology. Most preferably, the term "cubic nanoparticles" refers to a population of nanoparticles wherein at least 90% of the particles exhibit cubic morphology.

As used herein the terms "cubic NP" or "cubic nanoparticles" may also refer to nanoparticles each having 4-20 preferably 5-14 faces, facets or sides, wherein six of the faces, facets or sides comprise more than 40%, preferably more than 60%, most preferably more than 80% of the nanoparticle surface.

According to certain embodiments, the cubic nanoparticles comprise conductive metal cores. In other embodiments, the cubic nanoparticles comprise conductive metal alloy cores. Suitable non-limiting examples are metals of Au, Ag, Ni, Co, Pt, Pd, Cu, Al; and metal alloys of Au/Ag, Au/Cu, Au/Ag/Cu, Au/Pt, Au/Pd, Au/Ag/Cu/Pd, Pt—Rh, Ni—Co, and Pt—Ni—Fe.

According to the principles of the present invention, the cubic nanoparticle conductive cores are capped with an organic coating, wherein the organic coating comprises a backbone and at least a first functional moiety and a second functional moiety bound to said backbone, wherein the first functional moiety is further bound to the nanoparticle conductive cores.

The organic coating, according to the principles of the present invention, comprises a monolayer or multilayers of organic compounds. Suitable organic compounds are small molecules, monomers, oligomers or polymers. In currently preferred embodiments, the backbone of the organic coating comprises $C_3$-$C_{24}$ alkyl chains. The terms "backbone" or "backbone of the organic coating" as used herein refer to a contiguous chain of covalently bound atoms or moieties. According to the principles of the present invention this term further encompasses the incorporation of cyclic moieties including heterocyclic moieties in the contiguous chain. Non-limiting examples of organic chains encompassed by the term "backbone" include alkyl, aryl, alkylaryl, alkenyl, alkynyl, cycloalkyl, heterocyclyl, and heteroaryl chains.

Functional moieties suitable as the first functional moiety which is directly bound to the conductive core include, but are not limited to, a thiol, a thiolate, a sulfide, a disulfide, a sulfite, a sulfate, a carbamate, an amine, a phosphine, a carboxylate, a cyanate or an isocyanate moiety.

Non-limiting examples of organic coating backbones that are further modified with a first functional moiety include alkylthiols, e.g., alkylthiols with $C_3$-$C_{24}$ chains, arylthiols, alkylarylthiols, alkylthiolates, ω-functionalized alkylthiolates, arenethiolates, (γ-mercaptopropyl)tri-methyloxysilane, dialkyl sulfides, diaryl sulfides, alkylaryl sulfides, dialkyl disulfides, diaryl disulfides, alkylaryl disulfides, alkyl sulfites, aryl sulfites, alkylaryl sulfites, alkyl sulfates, aryl sulfates, alkylaryl sulfates, xanthates, oligonucleotides, polynucleotides, dithiocarbamate, alkyl amines, aryl amines, diaryl amines, dialkyl amines, alkylaryl amines, arene amines, alkyl phosphines, dialkyl phosphines, aryl phosphines, diaryl phosphines, alkylaryl phosphines, dialkyl phosphines, diaryl phosphines, alkylaryl phosphines, phosphine oxides, alkyl carboxylates, aryl carboxylates, dialkyl carboxylates, diaryl carboxylates, alkylaryl carboxylates, dialkyl carboxylates, diaryl carboxylates, alkylaryl carboxylates, cyanates, isocyanates, alkenyl thiols, alkynyl thiols, cycloalkyl thiols, heterocyclyl thiols, heteroaryl thiols, alkenyl thiolates, alkynyl thiolates, cycloalkyl thiolates, heterocyclyl thiolates, heteroaryl thiolates, alkenyl sulfides, alkynyl sulfides, cycloalkyl sulfides, heterocyclyl sulfides, heteroaryl sulfides, alkenyl disulfides, alkynyl disulfides, cycloalkyl disulfides, heterocyclyl disulfides, heteroaryl disulfides, alkenyl sulfites, alkynyl sulfites, cycloalkyl sulfites, heterocyclyl sulfites, heteroaryl sulfites, alkenyl sulfates, alkynyl sulfates, cycloalkyl sulfates, heterocyclyl sulfates, heteroaryl sulfates, alkenyl amines, alkynyl amines, cycloalkyl amines, heterocyclyl amines, heteroaryl amines, alkenyl carboxylates, alkynyl carboxylates, cycloalkyl carboxylates, heterocyclyl carboxylates, heteroaryl carboxylates, and combinations and derivatives thereof. It is to be understood that the organic coating backbones that are further modified with a first functional moiety, according to the principles of the present invention, must have at least one other functional moiety attached thereto to allow detection of explosive materials and fragments thereof. Hence, the organic coating comprises an organic backbone and at least a first functional moiety and a second functional moiety, wherein said functional moieties are attached to the organic backbone. According to the principles of the present invention, the functional moieties can be located at any position along the backbone of the organic coating. In a currently preferred embodiment, the organic coating comprises two functional moieties located at opposite ends of the backbone of the organic coating.

Suitable second functional moiety include, but is not limited to, an amine, an imine, an amide, an ammonium, a keto, an alcohol, an ester, a cyclodextrin, a phosphate, a thiol, a sulfonate, a sulfonyl and a carboxyl moiety. In particular, exemplary functional groups include, but are not limited to, ethyleneimine, aniline-boronic acid, diethyl ester, 2,5-dimercaptoterephthalic acid, n-(3-trifluoroethanesulfonyloxypropyl)-anthraquinone-2-carboxamide, thiophene, 1-[4-(4-dimethylamino-phenylazo)-3-[3,5-bis[3,5-bis[3,5-bis(3-butene-1-oxy)benzyloxy]benzyloxy]benzyloxy]phenyl]-2,2,2 trifluoroethanone, permethylated α-cyclodextrin-$6^A$-monoalcohol nitrate, dinitrophenyl substituted β-cyclodextrin, β- and γ-CD bearing a 4-amino-7-nitrobenz-2-oxa-1,3-diazole, sulfated and carboxymethylated β-cyclodextrins, mono(6-cyclohexylamino-6-deoxy)-β-cyclodextrin, mono(6-benzyl-imino-6-deoxy)-β-cyclodextrin, mono [6-(o-aminophenyl)imino-6-deoxy]-β-cyclodextrin, mono [6-(p-aminophenyl)imino-6-deoxy]-β-cyclodextrin, mono [6-(α-naphthyl)imino-6-deoxy]-β-cyclodextrin, hexakis(6-O-benzoyl)-α-cyclodextrin, heptakis(2,3,6-tri-O-benzoyl)-β-cyclodextrin, hexakis(2,3-di-O-benzyl)-α-cyclodextrin, hexakis(6-O-benzoyl-2,3-di-O-benzyl)-α-cyclodextrin, 2- and 6-amino-β-cyclodextrin, 2A,3A-alloepithio-2A,3A-dideoxy-β-cyclodextrin and combinations thereof.

An "alkyl" group refers to a saturated aliphatic hydrocarbon, including straight-chain, branched-chain and cyclic alkyl groups. In one embodiment, the alkyl group has 1-12 carbons designated here as $C_1$-$C_{12}$-alkyl. In another embodiment, the alkyl group has 1-6 carbons designated here as $C_1$-$C_6$-alkyl. In another embodiment, the alkyl group has 1-4 carbons designated here as $C_1$-$C_4$-alkyl. In a currently preferred embodiment, the alkyl group has 3-24 carbons designated here as $C_3$-$C_{24}$-alkyl. The alkyl group may be unsubstituted or substituted by one or more groups selected from halogen, haloalkyl, acyl, amido, ester, cyano, nitro, and azido.

A "cycloalkyl" group refers to a non-aromatic mono- or multicyclic ring system. In one embodiment, the cyclo-alkyl group has 3-10 carbon atoms. In another embodiment, the cyclo-alkyl group has 5-10 carbon atoms. Exemplary monocyclic cycloalkyl groups include cyclopentyl, cyclohexyl, cycloheptyl and the like. An alkylcycloalkyl is an alkyl group as defined herein bonded to a cycloalkyl group as defined herein. The cycloalkyl group can be unsubstituted or substituted with any one or more of the substituents defined above for alkyl.

An "alkenyl" group refers to an aliphatic hydrocarbon group containing a carbon-carbon double bond including straight-chain, branched-chain and cyclic alkenyl groups. In one embodiment, the alkenyl group has 2-8 carbon atoms. In another embodiment, the alkenyl group has 2-4 carbon atoms in the chain. Exemplary alkenyl groups include ethenyl, propenyl, n-butenyl, i-butenyl, 3-methylbut-2-enyl, n-pentenyl, heptenyl, octenyl, cyclohexyl-butenyl and decenyl. An alkylalkenyl is an alkyl group as defined herein bonded to an alkenyl group as defined herein. The alkenyl group can be unsubstituted or substituted through available carbon atoms with one or more groups defined hereinabove for alkyl.

An "alkynyl" group refers to an aliphatic hydrocarbon group containing a carbon-carbon triple bond including straight-chain and branched-chain. In one embodiment, the alkynyl group has 2-8 carbon atoms in the chain. In another embodiment, the alkynyl group has 2-4 carbon atoms in the chain. Exemplary alkynyl groups include ethynyl, propynyl, n-butynyl, 2-butynyl, 3-methylbutynyl, n-pentynyl, heptynyl, octynyl and decynyl. An alkylalkynyl is an alkyl group as defined herein bonded to an alkynyl group as defined herein. The alkynyl group can be unsubstituted or substituted through available carbon atoms with one or more groups defined hereinabove for alkyl.

An "aryl" group refers to an aromatic monocyclic or multicyclic ring system. In one embodiment, the aryl group has 6-10 carbon atoms. The aryl is optionally substituted at least one "ring system substituents" and combinations thereof, and are as defined herein. Exemplary aryl groups include phenyl or naphthyl. An alkylaryl is an alkyl group as defined herein bonded to an aryl group as defined herein. The aryl group can be unsubstituted or substituted through available carbon atoms with one or more groups defined hereinabove for alkyl.

A "heteroaryl" group refers to a heteroaromatic system containing at least one heteroatom ring wherein the atom is selected from nitrogen, sulfur and oxygen. The heteroaryl contains 5 or more ring atoms. The heteroaryl group can be monocyclic, bicyclic, tricyclic and the like. Also included in this definition are the benzoheterocyclic rings. Non-limiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group can be unsubstituted or substituted through available atoms with one or more groups defined hereinabove for alkyl.

A "heterocyclic ring" or "heterocyclyl" group refers to a five-membered to eight-membered rings that have 1 to 4 heteroatoms, such as oxygen, sulfur and/or in particular nitrogen. These five-membered to eight-membered rings can be saturated, fully unsaturated or partially unsaturated, with fully saturated rings being preferred. Preferred heterocyclic rings include piperidinyl, pyrrolidinyl pyrrolinyl, pyrazolinyl, pyrazolidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, and the like. An alkylheterocyclyl is an alkyl group as defined herein bonded to a heterocyclyl group as defined herein. The heterocyclyl group can be unsubstituted or substituted through available atoms with one or more groups defined hereinabove for alkyl.

"Ring system substituents" refer to substituents attached to aromatic or non-aromatic ring systems including, but not limited to, H, halo, haloalkyl, ($C_1$-$C_8$)alkyl, ($C_2$-$C_3$)alkenyl, ($C_2$-$C_8$)alkynyl, ($C_6$-$C_{10}$)aryl, acyl, amido, ester, cyano, nitro, azido, and the like.

A "halogen" or "halo" group refers to chlorine, bromine, fluorine, and iodine. The term "haloalkyl" refers to an alkyl group having some or all of the hydrogens independently replaced by a halogen group including, but not limited to, trichloromethyl, tribromomethyl, trifluoromethyl, triiodomethyl, difluoromethyl, chlorodifluoromethyl, pentafluoroethyl, 1,1-difluoroethyl bromomethyl, chloromethyl, fluoromethyl, iodomethyl, and the like.

An "amine" moiety refers to an —NRR' group, wherein R and R' are independently selected from hydrogen, alkyl and aryl. A currently preferred amine group is —NH$_2$. An "alkylamine" group is an alkyl group as defined herein bonded to an amine group as defined herein.

An "imine" moiety refers to an —NRR' group containing a carbon-nitrogen double bond wherein R and R' are independently selected from hydrogen, alkyl and aryl. An "alkylimine" group is an alkyl group as defined herein bonded to an imine group as defined herein.

An "amide" moiety refers to a —C(O)NRR' group wherein R and R' are independently selected from hydrogen, alkyl and aryl. An "alkylamide" group is an alkyl group as defined herein bonded to an amide group as defined herein.

An "ammonium" moiety refers to —NH$_4^+$ group.

An "acyl" moiety encompasses groups such as, but not limited to, formyl, acetyl, propionyl, butyryl, pentanoyl, pivaloyl, hexanoyl, heptanoyl, octanoyl, nonanoyl, decanoyl, undecanoyl, dodecanoyl, benzoyl and the like. Currently preferred acyl groups are acetyl and benzoyl.

A "thio" or "thiol" moiety refers to —SH group or, if between two other groups, —S—. A "thioalkyl" group is an alkyl group as defined herein bonded to a thiol group as defined herein.

A "sulfonyl" or "sulfone" moiety refers to —S(O)$_2$— group. An "alkylsulfone" group is an alkyl group as defined herein bonded to a sulfonyl group as defined herein.

A "sulfonate" moiety refers to a —S(O)$_2$O— group.

A "carboxy" or "carboxyl" moiety refers carboxylic acid and derivatives thereof including in particular, ester derivatives and amide derivatives. A "carboxyalkyl" group is an alkyl group as defined herein bonded to a carboxy group as defined herein.

A "carboxylate" moiety refers to a —COO$^-$ group, optionally having a positively charged counter ion present.

A "keto" moiety refers to a —C(O)— group.

An "alcohol" moiety refers to an —OH group including in particular sugar alcohols (cyclodextrin) and sugar acids.

A "phosphate" moiety refers to a PO$_4$ group wherein the bond to the parent moiety is through the oxygen atoms.

Another advantage for the use of cubic NPCOCs for sensing applications is increased sensitivity. This is mainly attributed to the three dimensional assembly of structures which provide a framework for signal amplifications.

According to certain embodiments, the sensors of the present invention are manufactured through a self-assembly process to produce films comprising cubic NPCOCs. The term "self-assembly" as used herein refers to a process of organization of molecules without intervening from an outside source. The self-assembly process takes place in a solution/solvent or directly on the solid-state substrate. The term "film", as used herein, corresponds to a configuration of well-arranged assembly of cubic NPCOCs, wherein each facet of a given cubic NPCOC is essentially in full contact with a facet of one of the other surrounding cubic NPCOCs. In this configuration, the fraction of voids between adjacent cubic nanoparticles is minimized (FIG. 1B). In contrast, the fraction of voids between adjacent spherical nanoparticles in films composed of SNPCOCs is significantly larger (FIG. 1A).

The synthesis of cubic NPCOCs is induced at the supersaturated regime along with selective adsorption of the capping agents (Lisiecki, *J. Phys. Chem. B*, 2005, 109: 12231). The synthesis can further be exemplified by either one of the following procedures:

i. Cubic platinum (Pt) nanoparticles capped with an organic coating are synthesized by bubbling hydrogen gas through an aqueous solution containing K$_2$PtCl$_4$ in the presence of the polymer used as capping material (El-Sayed et al., *Chem. Mater.*, 1996, 8: 1161).

ii. Cubic gold (Au) nanoparticles are grown using gentle reduction of the metal salt HAuCl$_4$ on a 3.5 nm gold seed used as a nucleation center. The process is performed with a large excess of a weak reducing agent (L-ascorbic acid) in the presence of a stabilizing agent (CTAB) according to Murphy et al. (*J. Am. Chem. Soc.*, 2004, 126: 8648). In this manner, the growth of cubic nanoparticles is well-controlled resulting in nanoparticles with dimensions of approximately 50-60 nm. Smaller cubic nanoparticles are further synthesized through a modification of this procedure. The cubic nanoparticles synthesized by this procedure are fairly mono-disperse nanoparticles and are obtained in excellent yield.

Without being bound by any theory or mechanism of action, the sensing signal from a sensing device composed of nanoparticles capped with an organic coating (NPCOC) can be obtained either by controlled aggregation (self-assembly) or by swelling of the NPCOC mainly through hydrogen-bonding. Other interactions, which include π-π, van-der-Waals, electrostatic, charge-transfer, or host-guest interactions, may also contribute to this process. To improve signal to noise ratios by self-assembly or by swelling, various parameters can be manipulated, for instance, nanoparticles and/or aggregate size, inter-particle distance, composition, periodicity, and aggregate thermal stability. Changes in permittivity usually occur in thin films having regions of discontinuities in chemiresistors, chemicapacitors and electrochemical cells which are composed of 2D or 3D films of metallic nanoparticles.

Exemplary methods for obtaining well-ordered two or three dimensional assemblies of cubic NPCOCs include, but are not limited to, i. Random deposition from solution of cubic NPCOCs on solid surfaces. The deposition is performed by drop casting, spin coating, spray coating and other similar techniques.

ii. Field-enhanced or molecular-interaction-induced deposition from solution of cubic NPCOCs on solid surfaces.

iii. Langmuir-Blodgett or Langmuir-Schaefer techniques. The substrate is vertically plunged through self-organized/well-ordered 2D monolayer of cubic NPCOCs at the air-subphase interface, wherein the latter being subsequently transferred onto it. Multiple plunging of the substrate through the 2D monolayer of cubic NPCOCs at the air-subphase interface, results in the fabrication of the 3D-ordered multilayers of cubic NPCOCs.

iv. Soft lithographic techniques, such as micro-contact printing (mCP), replica molding, micro-molding in capillaries (MIMIC), and micro-transfer molding (mTM). These methods are based on variations of self-assembly and replica molding of organic molecules and polymeric materials, for fabricating cubic NPCOCs from nanometer-scale to a mesoscopic scale (Whitesides et al., *J. Mater. Chem.*, 1997, 7: 1069).

v. Various combinations of Langmuir-Blodgett or Langmuir-Schaefer methods with soft lithographic techniques can be used to produce patterned Langmuir-Blodgett films of molecularly modified cubic NPCOCs which are transferred onto solid substrates.

vi. Printing on solid-state or flexible substrates using an inject printer designated for printed electronics. A solution containing the cubic NPCOCs is used as a filling material (or "ink") of the printing head according to procedures well known in the art as described in e.g. Holland et al. (*Ink Maker*, 2005, 8: 83).

Assemblies/films of cubic NPCOCs can be used as an array of sensors in conjunction with pattern recognition algorithms. Designing sensing-array elements have several advantages. The wide variety of ligands and synthetically-controlled structures provide the fabrication of chemically responsive yet distinctively different sensors. Through modifying the binding characters (e.g., non-covalent, hydrogen bonding, coordination, etc.) of the capping film and linker molecules, tunable molecular interactions and consequently enhanced selectivity can be achieved. Moreover, 3D assembly of the cubic structures provide controlled framework for signal amplifications. Coupling of nano-structures to solid substrates further provides easy array integration, rapid responses, and low power-driven portable devices.

In certain embodiments, the apparatus of the present invention comprises at least one sensor of cubic nanoparticles capped with an organic coating for the detection of specific volatile and non-volatile explosive compounds. In particular embodiments, the apparatus of the present invention comprises an array of sensors of cubic nanoparticles capped with an organic coating. The array of sensors comprises a plurality of sensors between 2 to 1000 sensors, more preferably between 2 to 500 sensors, even more preferably between 2 to 250 sensors, and most preferably between 2 to 125 sensors in an array.

In some embodiments, the present invention provides a sensing apparatus in which the cubic NPCOC sensors are used in conjunction with either one of a chemiresistor, chemicapacitor, quartz crystal microbalance, bulk acoustic wave (BAW) and surface acoustic wave (SAW) resonator, electrochemical cell, surface plasmon resonance (SPR), and optical spectroscope.

According to the principles of the present invention, sensing responses upon exposure of the sensors to an explosive material or fragment thereof may be induced through a change in conductivity, resistance, impedance, capacitance, inductance, or optical properties of one or more of the sensors.

For electronically induced sensing, electrical contacts of the deposited films of cubic NPCOCs can be performed by methods well known in the art. Suitable methods include, but are not limited to, photolithography, e-beam lithography, Focused Ion Beam (FIB), direct evaporation/sputtering through shadow mask, soft (stamp) contact, inject printing techniques of conductive nanoparticles, and other similar techniques. Alternatively, films of nanoparticles can be deposited on ready-made contacts that were fabricated by the either one of the methods described hereinabove. In certain embodiments, the nano-structures are coupled to solid-state substrates in order to provide easy array integration, rapid responses, and low power-driven portable format.

Figure 2:
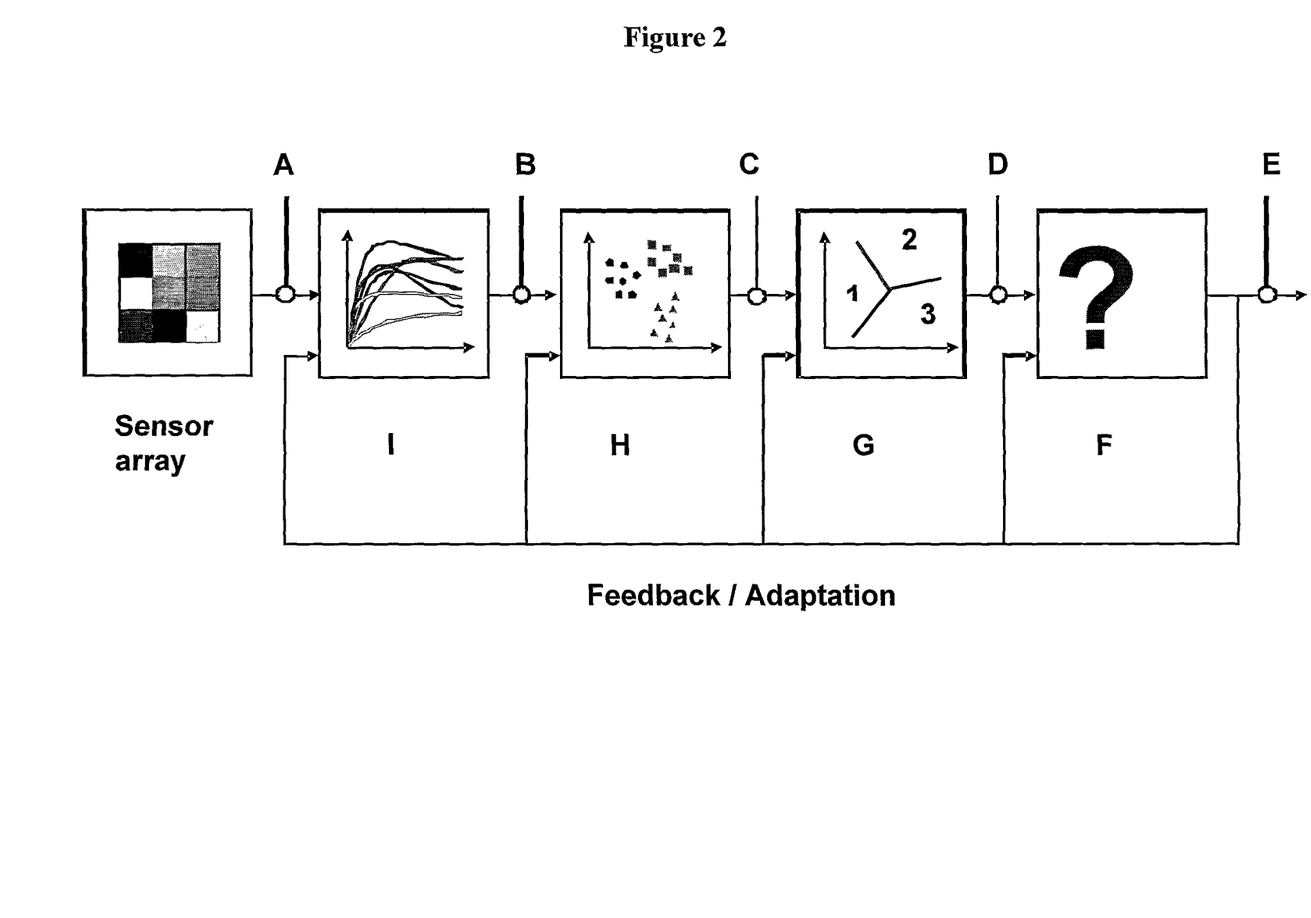
FIG. 2. A schematic diagram which illustrates the differentiation between odorants using an array of broadly cross reactive sensors, in which each individual sensor responds to a variety of odorants, in conjugation with learning and pattern recognition algorithms to allow classification. 'A'—raw measurements, 'B'—normalized measurements, 'C'—feature vector, 'D'—odor class (confidence level), 'E'—post processed odor class, 'F'—decision making, 'G'—classification, 'H'—dimensionality reduction, and 'I'—signal preprocessing.

Within the scope of the present invention are methods for determining at least one of the composition and concentration of volatile and non-volatile compounds derived from explosive materials in a sample. The methods comprise exposing the sensors of cubic NPCOCs to a sample and using pattern recognition algorithms in order to identify and possibly quantify explosive compounds in a given sample. Thus, provided herein is a system comprising the apparatus of the present invention in conjunction with a learning and pattern recognition analyzer. The analyzer receives output signals or patterns from the apparatus and analyses them by various pattern recognition algorithms to produce an output signature. By sorting an unknown signature using a database of stored or known signatures, desired compounds can be identified. According to the principles of the present invention, sensing is obtained through adsorption of volatile and non-volatile compounds to provide signal changes which are then conveyed to a learning and pattern recognition analyzer to generate identification of desired compounds. FIG. 2 schematically illustrates the differentiation between odorants using the system of the present invention. Particularly, the array of sensors is exposed to a variety of volatile and non-volatile compounds to provide a response (either electronic or optical) vs. time ($2^{nd}$ box on the left). The dimensionality is then reduced wherein the data is represented by a new basis set ($f_2$ vs. $f_1$; $3^{rd}$ box on the left). This representation allows to classify the different odors (1, 2 & 3; $4^{th}$ box on the left). The procedure can be iteratively performed until satisfactory odor classification is achieved.

Algorithms for sample analysis, suitable for identifying and possibly quantifying volatile and non-volatile compounds using the apparatus and system of the present invention include, but are not limited to, principal component analysis, Fischer linear analysis, neural network algorithms, genetic algorithms, fuzzy logic pattern recognition, and the like. After analysis is completed, the resulting information can, for example, be displayed on display, transmitted to a host computer, or stored on a storage device for subsequent retrieval.

Many of the algorithms are neural network based algorithms. A neural network has an input layer, processing layers and an output layer. The information in a neural network is distributed throughout the processing layers. The processing layers are made up of nodes that simulate the neurons by the interconnection to their nodes.

When a neural network is combined with a sensor array, the sensor data is propagated through the networks. In this manner, a series of vector matrix multiplications are performed and unknown analytes can be readily identified and determined. The neural network is trained by correcting the false or undesired outputs from a given input. Similar to statistical analysis revealing underlying patterns in a collection of data, neural networks locate consistent patterns in a collection of data, based on predetermined criteria.

Suitable pattern recognition algorithms include, but are not limited to, principal component analysis (PCA), Fisher linear discriminant analysis (FLDA), soft independent modeling of class analogy (SIMCA), K-nearest neighbors (KNN), neural networks, genetic algorithms, fuzzy logic, and other pattern recognition algorithms. In some embodiments, the Fisher linear discriminant analysis (FLDA) and canonical discriminant analysis (CDA) as well as combinations thereof are used to compare the output signature and the available data from the database.

In other embodiments, principal component analysis is used. Principal component analysis (PCA) involves a mathematical technique that transforms a number of correlated variables into a smaller number of uncorrelated variables. The smaller number of uncorrelated variables is known as principal components. The first principal component or eigenvector accounts for as much of the variability in the data as possible, and each succeeding component accounts for as much of the remaining variability as possible. The main objective of PCA is to reduce the dimensionality of the data set and to identify new underlying variables.

Principal component analysis compares the structure of two or more covariance matrices in a hierarchical fashion. For instance, one matrix might be identical to another except that each element of the matrix is multiplied by a single constant. The matrices are thus proportional to one another. More particularly, the matrices share identical eigenvectors (or principal components), but their eigenvalues differ by a constant. Another relationship between matrices is that they share principal components in common, but their eigenvalues differ. The mathematical technique used in principal component analysis is called eigenanalysis. The eigenvector associated with the largest eigenvalue has the same direction as the first principal component. The eigenvector associated with the second largest eigenvalue determines the direction of the second principal component. The sum of the eigenvalues equals the trace of the square matrix and the maximum number of eigenvectors equals the number of rows of this matrix.

The present invention provides a method to detect volatile and non-volatile compounds derived from explosive materials in a sample, comprising exposing the sensors of the apparatus to a sample and using pattern recognition algorithms in order to identify and possibly quantify the components of the sample.

In one embodiment, the present invention is used to detect minute concentrations of explosives or fragments thereof. In a currently preferred embodiment, the detection of volatile and non-volatile compounds derived from explosive materials is performed with sensitivity below one part per million (ppm). More preferably, the apparatus and system of the present invention detect volatile and non-volatile compounds derived from explosive materials with sensitivity of less than 100 parts per billion (ppb). Most preferably, the apparatus and system of the present invention detect volatile and non-volatile compounds derived from explosive materials with sensitivity of one part per billion (ppb) or less.

In some embodiments, the apparatus and system of the present invention comprise sensors which are designed to detect vapors of explosive compounds. In other embodiments, the apparatus and system of the present invention comprise sensors which are designed to detect non-volatile explosive compounds in the liquid state. In yet another embodiment, the apparatus and system of the present invention comprise sensors which are designed to detect mixtures of explosive compounds. In further embodiments, the apparatus and system of the present invention comprise sensors which are designed to detect decomposition fragments of explosive compounds.

In a currently preferred embodiment, the decomposition fragments which are derived from explosive materials are vapors including, but not limited to, nitric oxide (NO) and/or nitric dioxide ($NO_2$) gases. In certain embodiments, said apparatus and system comprise sensors which are designed to detect nitro-based explosives. In other embodiments, said apparatus and system comprise sensors which are designed to detect nitroso-based explosives.

In order to detect explosives, sensors are designed to adsorb compounds which are semi-volatile compounds, mostly polar in nature. The sensors of the present invention comprise cubic nanoparticles capped with an organic coating having a backbone to which at least two functional moieties are chemically bounded. The first functional moiety, according to the principles of the present invention, provides the attachment of the organic chains to the nanoparticle core whereas the second functional moiety is particularly designed for detecting explosives and fragments thereof.

According to the principles of the present invention, the second functional moiety has high affinity towards many explosive compositions. Explosives which can be detected by the apparatus and system of the present invention include, but are not limited to, pentaerythitol tetranitrate (PETN), tetranitro-tetrazacylooctane (HMX), nitroglycerin (NG), ethylene glycol dinitrate (EGDN), $NH_4NO_3$, o-nitrotoluene (2NT), m-nitrotoluene (3NT), p-nitrotoluene (4NT), dinitrotoluene (DNT), amino-dinitrotoluene (Am-DNT), trinitrotoluene (TNT), trinitrobenzene (TNB), dinitrobenzene (DNB), nitrobenzene (NB), methyl-2,4,6-trinitrophenylnitramine (Tetryl), picric acid, cyclotrimethylenetrinitramine (RDX), mixtures and fragments thereof. Examples of explosive mixtures are listed in Table 1.

TABLE 1

Typical mixtures of common explosive materials

| Explosive Mixture | Main composition |
| --- | --- |
| C-2 | RDX + TNT + DNT + NG |
| C-3 | RDX + TNT + DNT + Tetryl + NG |
| Cyclotol | RDX + TNT |
| Pentolite | PETN + TNT |
| PTX-1 | RDX + TNT + Tetryl |
| PTX-2 | RDX + TNT + PETN |
| Tetryol | TNT + Tetryl |
| Semtex-H | PETN + RDX |

Through modifying the second functional moiety enhanced selectivity towards different explosive compounds or mixtures thereof can be achieved.

It should be noted that, as used in this specification and the appended claims, the singular forms "a," "an," and "the" include plural referents unless the content clearly dictates otherwise. Thus, for example, reference to "an organic coating" includes a plurality of such organic coatings and equivalents thereof known to those skilled in the art, and so forth. It should also be noted that the term "or" is generally employed in its sense including "and/or" unless the content clearly dictates otherwise The principles of the present invention are demonstrated by means of the following non-limitative examples.

EXAMPLES

Example 1

Production of Au Cubic Nanoparticles Capped with an Organic Coating (Cubic NPCOCs)

The synthesis of cubic nanoparticles having dimensions of approximately 25-35 nm (FIG. 3A) was performed using a modified seed-mediated growth procedure, Specifically, gold seeds, having diameters of 1-3.5 nm, were synthesized using borohydride reduction of gold salt in the presence of CTAB as a capping agent. In a typical procedure, 0.25 ml of 0.01M $HAuCl_4.3H_2O$ solution was added to 7.5 ml of 0.1M CTAB solution. The solution was gently shaken, followed by the addition of 0.6 ml of an aqueous 0.01M $NaBH_4$ solution cooled down to ice temperatures, and rapid shaking for approximately 2 minutes. The solution was then stored at 25° C. for subsequent use.

Growth of cubic nanoparticles from Au seeds was performed by gentle reduction of the metal salt ($HAuCl_4$) on pre-prepared Au nucleation centers using a weak reducing agent (L-ascorbic acid) in the presence of a stabilizing agent, preferably CTAB. In particular, 0.2 ml of 0.01 M $HAuCl_4.3H_2O$ solution was added to a solution containing 8 ml of deionized water and 1.6 ml of 0.1M CTAB. The solution was gently mixed. Then, 0.95 ml of 0.1 M freshly prepared L-ascorbic acid solution was added. At this stage, the solution lost its orange color, indicating the reduction of $Au^{3+}$ to $Au^{1+}$. Further reduction of $Au^{1+}$ to $Au^0$ occurred upon mixing with 5 µl diluted (1:10) Au seed solution that was pre-aged for one hour. The growth medium was gently mixed and remained untouched for an hour or more. Finally, 1.5 ml of the solution was centrifuged for 15 minutes at 14,000 rpm to obtain the precipitate. The colorless supernatant was discarded. Rinsing of the precipitate was performed in 1.5 ml of deionized water followed by recentrifugation at 14,000 rpm. The precipitate was then redispersed in a suitable volume of deionized water depending on its quantity. This procedure provided cubic nanoparticles with more than 90% yield.

In order to obtain nanoparticles with reduced dimensions (in the range of 1-25 nm), gentle tuning of the gold seed to metal salt ($HAuCl_4$) ratio followed by rapid quenching of the gold precipitates at the early stages of the growth reaction was performed. In general, the procedure included the following steps: fast centrifugation, fast cooling under −78° C., dilution with large volume of solvent and addition of quenching reagents.

The coating of synthesized cubic nanoparticles with organic molecules was performed as follows: the designated organic molecules were dispersed in solution at an overall concentration range of $10^{-5}$-$10^{-1}$ M, depending on the type and characteristics of the organic molecules. Adsorption of these molecules on the surfaces of the nanoparticles was performed by means of self-assembly.

Example 2

Characterization of Au Cubic Nanoparticles Capped with an Organic Coating (Cubic NPCOCs)

Figure 3A:
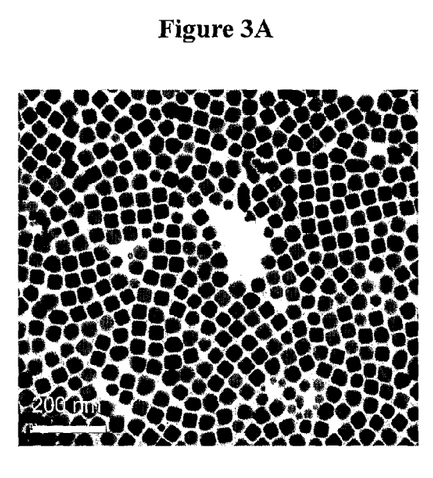
FIGS. 3A-3B. Transmission electron micrographs of cubic (3A) and spherical (3B) gold (Au) nanoparticles.
Figure 3B:
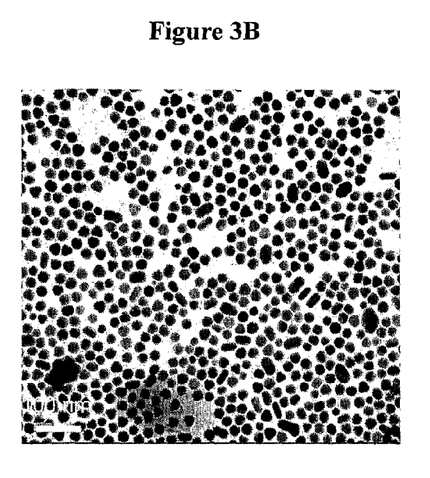
Figure 4:
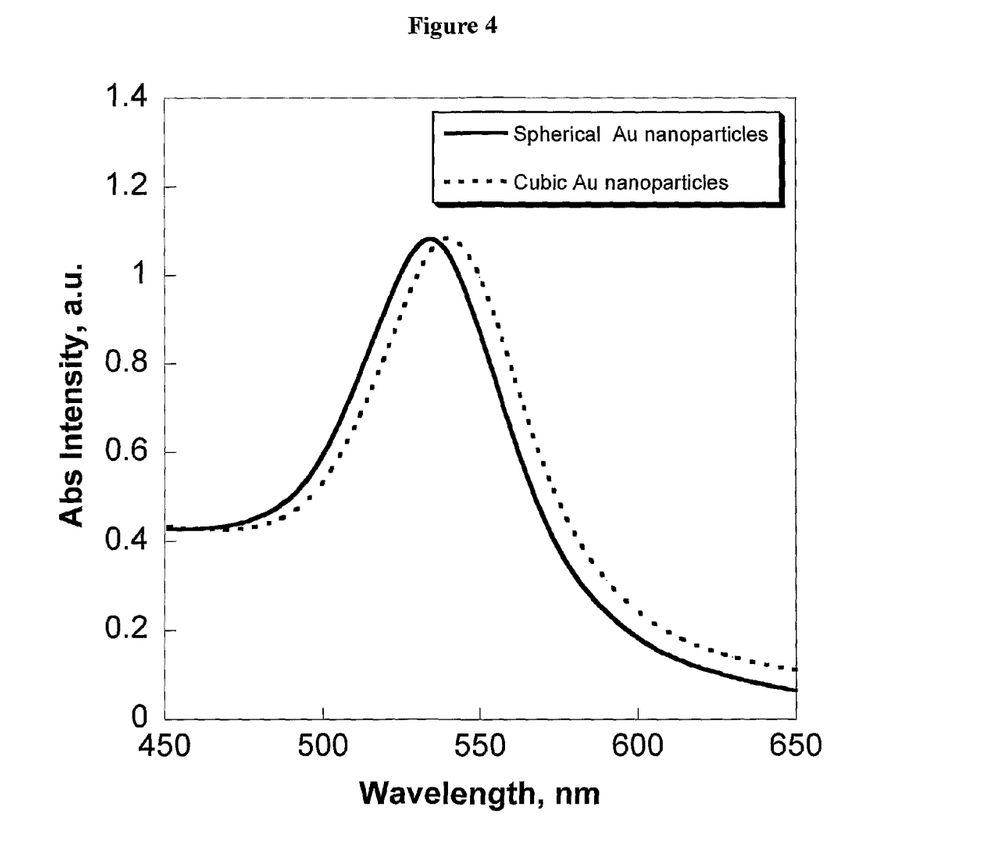
FIG. 4. Optical absorption spectra of solutions containing cubic (dotted line) and spherical (solid line) gold nanoparticles.

Transmission electron micrographs clearly show the cubic morphology of the gold nanoparticles of the present invention in comparison to the spherical nanoparticles (FIGS. 3A and 3B, respectively). The nanoparticles obtained were uniform in size and their dimensions ranged approximately between 25 to 35 nanometers. Optical absorption spectra of aqueous solutions containing 50 nm cubic and 25 nm spherical Au nanoparticles stabilized by bi-layer of CTAB surfactant are presented in FIG. 4 (dotted line and solid line, respectively). Nanoparticles possessing cubic morphology as well as nanoparticles possessing spherical morphology showed a single intense and sharp plasmon absorption band at approximately 535 nm. However, the plasmon absorption peak of the cubic Au nanoparticles was slightly red-shifted compared to that of the spherical ones. Without being bound by any theory or mechanism of action, this shift is attributed to the difference in nanoparticle size, wherein an increase in particle dimension positively correlates with a shift of the absorption band to longer wavelengths.

Example 3

Figure 5A:
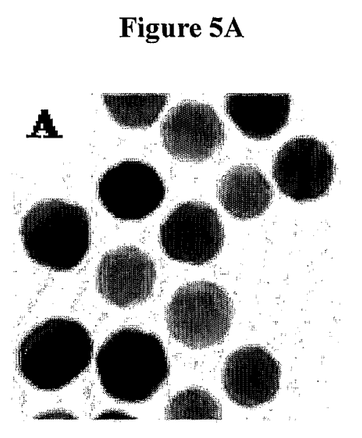
FIGS. 5A-5H. Transmission electron micrographs of gold nanoparticles precipitated from a solution dispersion after (5A) 1.5 minutes, (5B) 2.5 minutes, (5C) 3 minutes, (5D) 4 minutes, (5E) 6 minutes, (5F) 15 minutes, (5G) 1 hour, and (5H) one night. Each micrograph represents a 110×110 nm² square.
Figure 5B:
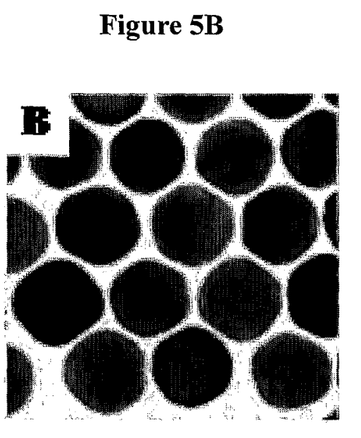
Figure 5C:
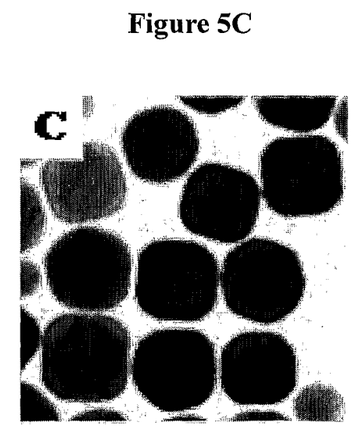
Figure 5D:
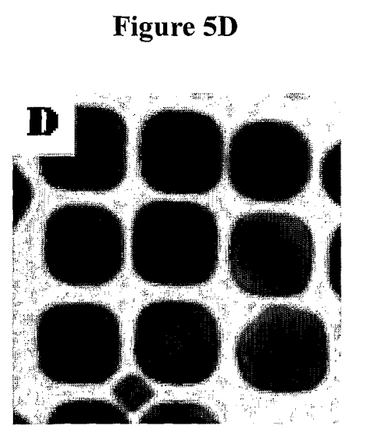
Figure 5E:
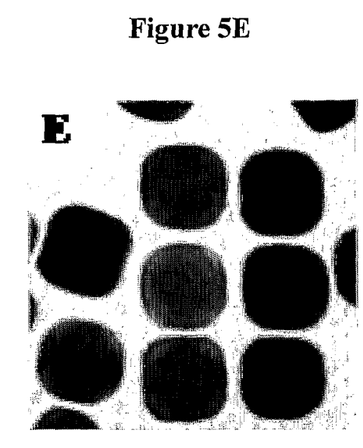
Figure 5F:
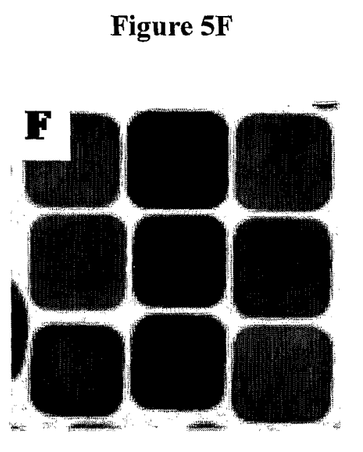
Figure 5G:
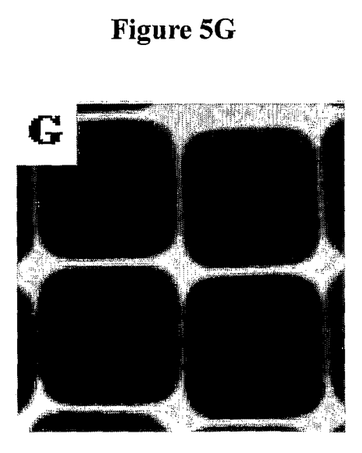
Figure 5H:
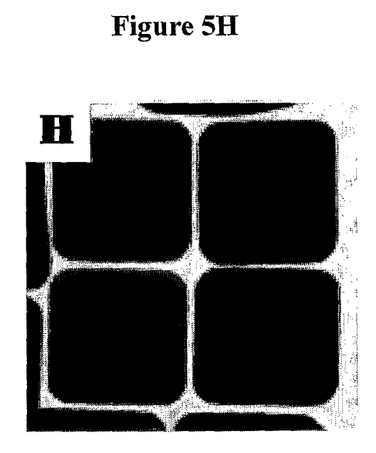

Morphology of Au Cubic Nanoparticles Capped with an Organic Coating (Cubic NPCOCs) at Different Stages of Growth Gold (Au) nanoparticles were quenched at different stages of the growth reaction and intermediate growth products were characterized (Haick & Dovgolevsky, *Small*, 2008, 4(11): 2059; published after the priority document IL 190475). Structural and morphological analysis indicated that nanocubes are formed in the following shape transformation sequence: quasi-spherical shapes are transformed to decahedrons, to cuboctahedrons, and finally to nanocubes. FIGS. 5A-5H show transmission electron micrographs of Au nanoparticles growth products obtained at different quenching times. Au seeds that were grown for 1.5 minutes showed 17-23 nm quasi-spherical shapes (FIG. 5A). After a reaction time of 2.5 minutes, over 92% of the quasi-spherical nanoparticles kept their shape (approximate sizes 25-27 nm; FIG. 5B). The remaining Au nanoparticles (less than 8%) transformed to cubic-like shapes having edge length of 25-27 nm. Increasing the reaction time to 3.0 and 4.0 minutes (FIGS. 5C and 5D, respectively) showed continuous disappearance of the quasi-spherical nanoparticles and evolution of further new nanocubes having 25-27 nm dimensions. Increasing the dispersion time from 6 to 15 to 60 minutes increased the size of the monodispersed nanocubes from 30±1 to 34±1 to 46±1 nm, respectively (FIGS. 5E, 5F and 5G). The nanocubes essentially ceased to grow after 24 hours dispersion time, yet they showed sharper corners than those grown at shorter dispersion times (FIG. 5H). These results were further confirmed based on similar shape transformation sequences for Pt, Pd, and Ag nanoparticles.

Example 4

Synthesis and Characterization of Pt Cubic Nanoparticles Capped with an Organic Coating (Cubic NPCOCs)

Polyacrylate-capped cubic Pt nanoparticles were prepared using the hydrogen reduction method of platinum salt ($K_2PtCl_4$) in water, as described in Narayanan & El-Sayed, *J. Phys. Chem. B*, 2003, 107: 12416. Specifically, 250 mL of deionized water (18 MΩ-cm) purified with a Millipore Nanopure water system, 2 mL of 0.01 M $K_2PtCl_4$, and 1 mL of 0.1 M sodium polyacrylate were mixed. The solution was adjusted to pH=9. After the solution was thoroughly mixed, argon was bubbled for 20 minutes and then hydrogen gas was bubbled for 5 minutes at flow rate of 0.6 l/min. The flask was then sealed, wrapped in aluminum foil, and stored in the dark for 24 hours. Large excess of dodecanethiol (20-fold excess, 10 µL) was added to 10 mL of THF/water solution containing Pt nanoparticles. After vigorous stirring of the solution for a few days, a few granules of KI as phase-transfer agent and 3 ml of toluene were added to the nanoparticle THF/water solution and vigorously shaken. The KI salt was added to induce phase transfer of dodecanethiol (DDT)-capped Pt nanoparticles to the toluene phase. After transferring the DDT-capped Pt nanoparticles to toluene, the organic phase was separated and washed with ethanol for removal of thiols excess.

Figure 6A:
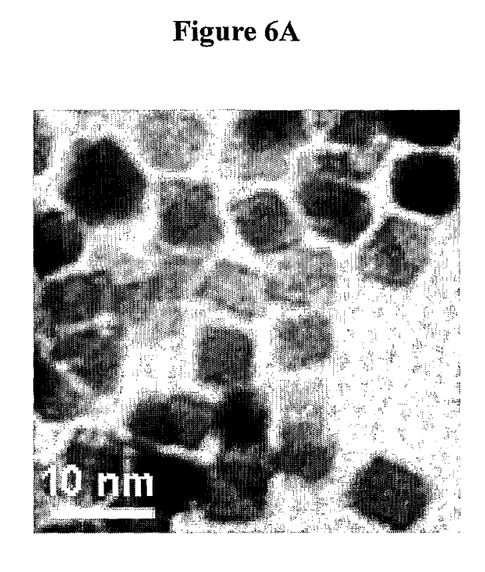
FIGS. 6A-6B. Transmission electron micrographs of DDT-capped cubic (6A) and spherical (6B) Pt nanoparticles.
Figure 6B:
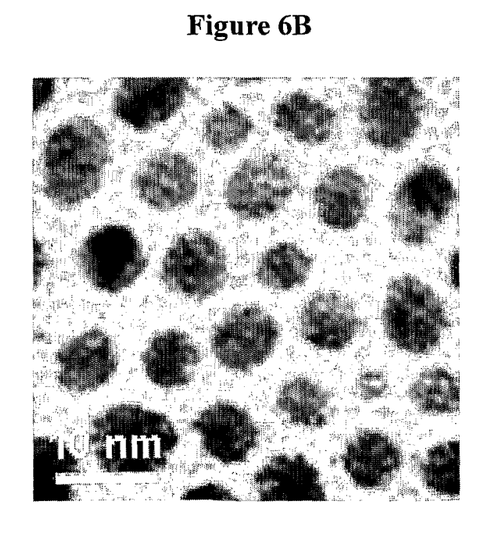

Transmission electron microscopy (TEM) analysis at different rotation angles of the TEM grid indicated that the voids between adjacent DTT-capped cubic Pt nanoparticles ranged between 0.8 nm for simple cubic nanoparticle assembly and approximately 0 nm for body centered cubic (bcc) arrangement. Importantly, the voids between adjacent cubic nanoparticles were significantly smaller than those of DDT-capped spherical Pt nanoparticles (FIGS. 6A and 6B, respectively).

Hence, it is clearly shown that cubic NPCOCs exhibit low fraction of voids in comparison to spherical NPCOCs. An apparatus which comprises an array of chemically sensitive cubic NPCOC sensors of the present invention, can provide a more pronounced optical as well as electrical response upon exposure to different vapors derived from explosive materials in comparison to spherical nanoparticle films. Without being bound by any theory or mechanism of action, this might be attributed to maximizing the physical and chemical contacts between adjacent nanoparticles which enables a more pronounced response upon exposure to explosives and vapors thereof. It is thus contemplated that cubic NPCOC sensors are more sensitive in detecting compounds derived from explosive materials in comparison to spherical NPCOC sensors.

Example 5

Fabrication of Chemiresistors Based on Pt Cubic Nanoparticles Capped with an Organic Coating (Cubic NPCOCs)

Chemiresistors based on Pt cubic nanoparticles capped with an organic coating were prepared by drop casting of nanoparticle solution on interdigitated microsensor electrode (IME, ABTECH) devices, combined from 25 pairs of gold electrodes of 20 μm width and 20 μM spacing on glass substrate (Dovgolevsky et al., *Small*; published online after the priority document IL 190475).

Example 6

Response Measurements of Sensors of Cubic Nanoparticles Capped with an Organic Coating (Cubic NPCOCs)

The developed sensors are mounted on a custom PTFE circuit board which had 10 separated sensor sites. The board is then mounted in a stainless steel test chamber with a volume of less than 100 cm$^3$. An Agilent Multifunction switch 34980 controlled by USB is used to choose the active sensor at a given time. A Stanford Research System SR830 DSP Lock-in amplifier that is controlled by an IEEE 488 system is used to supply the AC voltage signal and measure the corresponding current or resistance of the nanoparticle coating in IME. The sensing responses are obtained at fixed AV voltage (200 mV, 500 Hz). The entire system is controlled by a custom Labview program. Dry, purified, oil-free air, obtained from a compressed air source is used as a carrying gas for the volatile and non-volatile compounds to be detected. The compounds are vaporized by bubbling carrier gas through their liquid states. Partial pressures of the vapors of desired compounds are varied between 0.07 and 0.08 P/P°. The vapor-saturated air flow is diluted by air flow at a flow rate of 0.5 l/min.

In order to simulate the detection of explosives 4-(3-trifluoromethylazirino)benzoyl-N-succinimide-CH$_2$—CH=CH-capped (TDBA-OSu-CH$_2$—CH=CH-capped) and para-phenylenediamine-TDBA-OSu-CH$_2$—CH=CH-capped (PPD-TDBA-OSu-CH$_2$—CH=CH-capped) Au/Pt nanoparticles are exposed at each time to 10 ppb of NO and NO$_2$. NO and NO$_2$ gases are used to simulate explosive detection since they are the main compounds released from explosive materials. Therefore, detecting NO and NO$_2$ is indicative for the presence of explosives.

It is appreciated by persons skilled in the art that the present invention is not limited by what has been particularly shown and described hereinabove. Rather the scope of the present invention includes both combinations and sub-combinations of various features described hereinabove as well as variations and modifications. Therefore, the invention is not to be constructed as restricted to the particularly described embodiments, and the scope and concept of the invention will be more readily understood by references to the claims, which follow.

The invention claimed is:

1. An apparatus for detecting volatile and non-volatile compounds derived from explosive materials, comprising at least one chemically sensitive sensor comprising cubic nanoparticle conductive cores capped with an organic coating, wherein the organic coating comprises a backbone and at least a first functional moiety and a second functional moiety bound to said backbone, wherein the first functional moiety is further bound to the nanoparticle conductive cores, and wherein the second functional moiety comprises at least one of an amine, an imine, an amide, an ammonium, a keto, an alcohol, an ester, a cyclodextrin, a phosphate, a thiol, a sulfonate, a sulfonyl or a carboxyl moiety.

2. The apparatus according to claim 1, wherein the cubic nanoparticle conductive cores are selected from the group consisting of Au, Ag, Ni, Co, Pt, Pd, Cu, Al, Au/Ag, Au/Cu, Au/Ag/Cu, Au/Pt, Au/Pd, Au/Ag/Cu/Pd, Pt/Rh, Ni/Co, and Pt/Ni/Fe.

3. The apparatus according to claim 1, wherein the organic coating comprises a monolayer or multilayers of organic compounds, wherein the organic compounds are selected from small molecules, monomers, oligomers and polymers.

4. The apparatus according to claim 1, wherein the backbone of the organic coating comprises $C_3$-$C_{24}$ alkyl chains.

5. The apparatus according to claim 1, wherein the first functional moiety of the organic coating comprises a thiol, a thiolate, a sulfide, a disulfide, a sulfite, a sulfate, a carbamate, an amine, a phosphine, a carboxylate, a cyanate, or an isocyanate moiety.

6. The apparatus according to claim 1, wherein the second functional moiety of the organic coating is selected from the group consisting of ethyleneimine, aniline-boronic acid, diethyl ester, 2,5-dimercaptoterephthalic acid, n-(3-trifluoroethanesulfonyloxypropyl)-anthraquinone-2-carboxamide, thiophene, 1-[4-(4-dimethylamino-phenylazo)-3-[3,5-bis[3,5-bis[3,5-bis(3-butene-1-oxy)benzyloxy]benzyloxy]benzyloxy]phenyl]-2,2,2 trifluoroethanone, permethylated α-cyclodextrin-6$^4$-monoalcohol nitrate, dinitrophenyl substituted β-cyclodextrin, β- and γ-CD bearing a 4-amino-7-nitrobenz-2-oxa-1,3-diazole, sulfated and carboxymethylated β-cyclodextrins, mono(6-cyclohexylamino-6-deoxy)-β-cyclodextrin, mono(6-benzyl-imino-6-deoxy)-β-cyclodextrin, mono [6-(o-aminophenyl)imino-6-deoxy]-β-cyclodextrin, mono [6-(p-aminophenyl)imino-6-deoxy]-β-cyclodextrin, mono [6-(α-naphthyl)imino-6-deoxy]-β-cyclodextrin, hexakis(6-O-benzoyl)-α-cyclodextrin, heptakis(2,3,6-tri-O-benzoyl)-β-cyclodextrin, hexakis(2,3-di-O-benzyl)-α-cyclodextrin, hexakis(6-O-benzoyl-2,3-di-O-benzyl)-α-cyclodextrin, 2- and 6-amino-β-cyclodextrin, 2A,3A-alloepithio-2A,3A-dideoxy-β-cyclodextrin, and combinations thereof.

7. The apparatus according to claim 1, wherein the explosive materials to be detected are selected from the group consisting of pentaerythitol tetranitrate (PETN), tetranitrotetrazacylooctane (HMX), nitroglycerin (NG), ethylene glycol dinitrate (EGDN), NH$_4$NO$_3$, dinitrotoluene (DNT), trinitrotoluene (TNT), tetryl, picric acid, cyclotrimethylenetrinitramine (RDX), mixtures and fragments thereof.

8. The apparatus according to claim 1, wherein the cubic nanoparticles capped with an organic coating are in a configuration selected from 1D wires, 2D films and 3D assemblies.

9. The apparatus according to claim 1, further comprising at least one of a chemiresistor, chemicapacitor, quartz crystal microbalance, bulk acoustic wave (BAW) and surface acoustic wave (SAW) resonator, electrochemical cell, surface plasmon resonance (SPR), and optical spectroscope.

10. A system having:
(i) an apparatus for detecting volatile and non-volatile compounds derived from explosive materials comprising an array of chemically sensitive sensors comprising cubic nanoparticle conductive cores capped with an organic coating, wherein the organic coating comprises a backbone and at least a first functional moiety and a second functional moiety bound to said backbone, wherein the first functional moiety is further bound to the nanoparticle conductive cores, and wherein the second functional moiety comprises at least one of an amine, an imine, an amide, an ammonium, a keto, an alcohol, an ester, a cyclodextrin, a phosphate, a thiol, a sulfonate, a sulfonyl or a carboxyl moiety; and (ii) a learning and pattern recognition analyzer, wherein the learning and pattern recognition analyzer receives sensor output signals and compares them to stored data.

11. The system according to claim 10, wherein the cubic nanoparticle conductive cores are selected from the group consisting of Au, Ag, Ni, Co, Pt, Pd, Cu, Al, Au/Ag, Au/Cu, Au/Ag/Cu, Au/Pt, Au/Pd, Au/Ag/Cu/Pd, Pt/Rh, Ni/Co, and Pt/Ni/Fe.

12. The system according to claim 10, wherein the organic coating comprises a monolayer or multilayers of organic compounds, wherein the organic compounds are selected from small molecules, monomers, oligomers and polymers.

13. The system according to claim 10, wherein the backbone of the organic coating comprises $C_3$-$C_{24}$ alkyl chains.

14. The system according to claim 10, wherein the first functional moiety of the organic coating comprises a thiol, a thiolate, a sulfide, a disulfide, a sulfite, a sulfate, a carbamate, an amine, a phosphine, a carboxylate, a cyanate, or an isocyanate moiety.

15. The system according to claim 10, wherein the second functional moiety of the organic coating is selected from the group consisting of ethyleneimine, aniline-boronic acid, diethyl ester, 2,5-dimercaptoterephthalic acid, n-(3-trifluoroethanesulfonyloxypropyl)-anthraquinone-2-carboxamide, thiophene, 1-[4-(4-dimethylamino-phenylazo)-3-[3,5-bis[3,5-bis[3,5-bis(3-butene-1-oxy)benzyloxy]benzyloxy]benzyloxy]phenyl]-2,2,2 trifluoroethanone, permethylated α-cyclodextrin-$6^4$-monoalcohol nitrate, dinitrophenyl substituted β-cyclodextrin, β- and γ-CD bearing a 4-amino-7-nitrobenz-2-oxa-1,3-diazole, sulfated and carboxymethylated β-cyclodextrins, mono(6-cyclohexylamino-6-deoxy)-β-cyclodextrin, mono(6-benzyl-imino-6-deoxy)-β-cyclodextrin, mono [6-(o-aminophenyl)imino-6-deoxy]-β-cyclodextrin, mono [6-(p-aminophenyl)imino-6-deoxy]-β-cyclodextrin, mono [6-(α-naphthyl)imino-6-deoxy]-β-cyclodextrin, hexakis(6-O-benzoyl)-α-cyclodextrin, heptakis(2,3,6-tri-O-benzoyl)-β-cyclodextrin, hexakis(2,3-di-O-benzyl)-α-cyclodextrin, hexakis(6-O-benzoyl-2,3-di-O-benzyl)-α-cyclodextrin, 2- and 6-amino-β-cyclodextrin, 2A,3A-alloepithio-2A,3A-dideoxy-β-cyclodextrin, and combinations thereof.

16. The system according to claim 10, wherein the explosive materials to be detected are selected from the group consisting of pentaerythitol tetranitrate (PETN), tetranitrotetrazacylooctane (HMX), nitroglycerin (NG), ethylene glycol dinitrate (EGDN), $NH_4NO_3$, dinitrotoluene (DNT), trinitrotoluene (TNT), tetryl, picric acid, cyclotrimethylenetrinitramine (RDX), mixtures and fragments thereof.

17. The system according to claim 10, wherein the cubic nanoparticles capped with an organic coating are in a configuration selected from 1D wires, 2D films and 3D assemblies.

18. The system according to claim 10, further comprising at least one of a chemiresistor, chemicapacitor, quartz crystal microbalance, bulk acoustic wave (BAW) and surface acoustic wave (SAW) resonator, electrochemical cell, surface plasmon resonance (SPR), and optical spectroscope.

19. The system according to claim 10, wherein the learning and pattern recognition analyzer comprises at least one algorithm selected from the group consisting of artificial neural network algorithms, principal component analysis (PCA), multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor.

20. A method for detecting volatile and non-volatile compounds derived from explosive materials in a sample, comprising the steps of:
i) providing a system comprising an apparatus comprising an array of chemically sensitive sensors comprising cubic nanoparticle conductive cores capped with an organic coating, wherein the organic coating comprises a backbone and at least a first functional moiety and a second functional moiety bound to said backbone, wherein the first functional moiety is further bound to the nanoparticle conductive cores, and wherein the second functional moiety comprises at least one of an amine, an imine, an amide, an ammonium, a keto, an alcohol, an ester, a cyclodextrin, a phosphate, a thiol, a sulfonate, a sulfonyl or a carboxyl moiety; and further comprising a learning and pattern recognition analyzer, wherein the learning and pattern recognition analyzer receives sensor output signals from the apparatus and compares them to stored data,
ii) exposing the sensor array of the apparatus to the sample, and
iii) using a pattern recognition algorithm to detect the presence of volatile and non-volatile compounds derived from explosive materials in the sample.

21. The method according to claim 20, wherein the system further comprises at least one of a chemiresistor, chemicapacitor, quartz crystal microbalance, bulk acoustic wave (BAW) and surface acoustic wave (SAW) resonator, electrochemical cell, surface plasmon resonance (SPR), and optical spectroscope.

22. The method according to claim 20, wherein the learning and pattern recognition analyzer comprises at least one algorithm selected from the group consisting of artificial neural network algorithms, principal component analysis (PCA), multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor.

23. The method according to claim 20, wherein the explosive materials to be detected are selected from the group consisting of pentaerythitol tetranitrate (PETN), tetranitrotetrazacylooctane (HMX), nitroglycerin (NG), ethylene glycol dinitrate (EGDN), $NH_4NO_3$, dinitrotoluene (DNT), trinitrotoluene (TNT), tetryl, picric acid, cyclotrimethylenetrinitramine (RDX), mixtures and fragments thereof.

* * * * *